(12) United States Patent
Abiven et al.

(10) Patent No.: US 12,279,839 B2
(45) Date of Patent: Apr. 22, 2025

(54) END EFFECTOR FOR ROBOTIC SHOULDER ARTHROPLASTY

(71) Applicant: Orthosoft ULC, Montreal (CA)

(72) Inventors: Jean-Guillaume Abiven, Montreal (CA); Karine Dupuis, Montreal (CA); Trong-Tin Nguyen, Laval (CA)

(73) Assignee: Orthosoft ULC, Montreal (CA)

(*) Notice: Subject to any disclaimer, the term of this patent is extended or adjusted under 35 U.S.C. 154(b) by 602 days.

(21) Appl. No.: 17/224,841

(22) Filed: Apr. 7, 2021

(65) Prior Publication Data

US 2021/0330402 A1 Oct. 28, 2021

Related U.S. Application Data

(60) Provisional application No. 63/015,217, filed on Apr. 24, 2020.

(51) Int. Cl.
| | |
|---|---|
| *A61B 34/30* | (2016.01) |
| *A61B 17/16* | (2006.01) |
| *A61B 34/00* | (2016.01) |
| *A61B 34/20* | (2016.01) |
| *A61B 17/00* | (2006.01) |
| *A61B 17/56* | (2006.01) |

(Continued)

(52) U.S. Cl.
CPC .......... *A61B 34/30* (2016.02); *A61B 17/1684* (2013.01); *A61B 34/20* (2016.02); *A61B 34/25* (2016.02); *A61B 2017/00477* (2013.01); *A61B 2017/564* (2013.01); *A61B 2034/107* (2016.02); *A61B 2034/2057* (2016.02); *A61B 90/03* (2016.02)

(58) Field of Classification Search
CPC .......... A61B 17/16–17/1697; A61B 2034/305
See application file for complete search history.

(56) References Cited

U.S. PATENT DOCUMENTS

| | | | | | |
|---|---|---|---|---|---|
| 5,697,939 | A | * | 12/1997 | Kubota | .................. A61B 90/50 606/130 |
| 5,824,007 | A | * | 10/1998 | Faraz | .................. F16M 11/046 600/102 |
| 9,668,768 | B2 | * | 6/2017 | Piron | ..................... A61B 34/30 |

(Continued)

FOREIGN PATENT DOCUMENTS

| | | |
|---|---|---|
| CA | 3115911 C | 1/2024 |
| CN | 113545850 A | 10/2021 |

(Continued)

OTHER PUBLICATIONS

"Australian Application Serial No. 2021202326, First Examination Report mailed Dec. 2, 2021", 5 pgs.

(Continued)

*Primary Examiner* — Zade Coley
(74) *Attorney, Agent, or Firm* — SCHWEGMAN LUNDBERG & WOESSNER, P.A.

(57) ABSTRACT

A robotic surgical system can include an end effector coupled to a robotic arm. A reamer operable to ream bone can be coupled to the end effector (e.g., via a retainer). The reamer can include a primary driveshaft and a cutting head. The primary driveshaft can be rotatable about a first axis of rotation and the cutting head can be rotatable about a second axis of rotation, for example parallel to and offset from the first axis of rotation.

13 Claims, 13 Drawing Sheets

(51) Int. Cl.
  *A61B 34/10* (2016.01)
  *A61B 90/00* (2016.01)

(56) References Cited

U.S. PATENT DOCUMENTS

| | | | |
|---|---|---|---|
| 9,814,471 | B2 | 11/2017 | Goldberg et al. |
| 2007/0089557 | A1* | 4/2007 | Solomon ............... A61B 34/71 74/490.01 |
| 2008/0147070 | A1* | 6/2008 | Michel ............... A61B 17/1624 606/80 |
| 2008/0287952 | A1 | 11/2008 | Mcminn et al. |
| 2011/0015647 | A1* | 1/2011 | Salisbury, Jr. ....... B25J 19/0004 606/130 |
| 2011/0082462 | A1* | 4/2011 | Suarez .................. A61B 90/03 606/130 |
| 2013/0035696 | A1 | 2/2013 | Qutub |
| 2013/0184863 | A1 | 7/2013 | Isobe et al. |
| 2014/0039517 | A1 | 2/2014 | Corporation |
| 2014/0276949 | A1 | 9/2014 | Staunton et al. |
| 2015/0119891 | A1* | 4/2015 | Goldberg ........... A61B 17/1631 606/80 |
| 2017/0312035 | A1 | 11/2017 | May et al. |
| 2018/0042620 | A1* | 2/2018 | Hopkins ............ A61B 17/1735 |

FOREIGN PATENT DOCUMENTS

| | | | | |
|---|---|---|---|---|
| WO | WO-2011041428 | A2 * | 4/2011 | ........... A61B 17/162 |
| WO | WO-2019079634 | A1 | 4/2019 | |

OTHER PUBLICATIONS

"Australian Application Serial No. 2021202326, Response filed Feb. 24, 2022 to First Examination Report mailed Dec. 2, 2021", 61 pgs.

"Australian Application Serial No. 2021202326, Response filed May 30, 2022 to Subsequent Examiners Report mailed Mar. 16, 2022", 16 pgs.

"Australian Application Serial No. 2021202326, Response filed Jul. 15, 2022 to Subsequent Examiners Report mailed Jun. 7, 2022", 17 pgs.

"Australian Application Serial No. 2021202326, Subsequent Examiners Report mailed Mar. 16, 2022". 4 pgs.

"Australian Application Serial No. 2021202326, Subsequent Examiners Report mailed Jun. 7, 2022", 3 pgs.

"Australian Application Serial No. 2021202326, Subsequent Examiners Report mailed Aug. 9, 2022", 3 pgs.

"Canadian Application Serial No. 3,115,911, Examiner's Rule 86(2) Requisition mailed Aug. 18, 2022", 4 pgs.

"European Application Serial No. 21170275.8, Extended European Search Report mailed Sep. 8, 2021", 8 pgs.

"European Application Serial No. 21170275.8, Response filed Mar. 31, 2022 to Extended European Search Report mailed Sep. 8, 2021", 27 pgs.

"Australian Application Serial No. 2021202326, Response filed Oct. 12, 2022 to Subsequent Examiners Report mailed Aug. 9, 2022", 20 pgs.

"Canadian Application Serial No. 3,115,911, Response filed Dec. 14, 2022 to Examiner's Rule 86 Requisition mailed Aug. 18, 2022", 18 pgs.

"Chinese Application Serial No. 202110441341.2, Office Action mailed Jan. 5, 2024" W/English Translation, 11 pgs.

"Chinese Application Serial No. 202110441341.2, Response filed Mar. 4, 2024 to Office Action mailed Jan. 5, 2024", W/ English claims, 14 pgs.

"Chinese Application Serial No. 202110441341.2, Office Action mailed May 8, 2024", w/ English translation, 6 pgs.

"Chinese Application Serial No. 202110441341.2, Response filed Jun. 24, 2024 to Office Action mailed May 8, 2024", w/ current English claims, 12 pgs.

* cited by examiner

END EFFECTOR FOR ROBOTIC SHOULDER ARTHROPLASTY

CLAIM OF PRIORITY

This application claims the benefit of U.S. Provisional Patent Application Ser. No. 63/015,217, filed on Apr. 24, 2020, the benefit of priority of which is claimed hereby, and which is incorporated by reference herein in its entirety.

BACKGROUND

During shoulder arthroplasty, a reamer or other cutting device can be used to shape a patient's bone surface, to prepare the bone to receive an implant. A reamer is typically guided by a guide pin. An incision is made in the shoulder region of a patient, into which the guide pin is inserted and affixed to the patient's bone surface. Cutting and shaping of the bone surface is then performed by rotating the reamer around the guide pin. A similar procedure can be utilized during replacement of other joints in the body, such to ream the acetabulum of a hip joint.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1A:
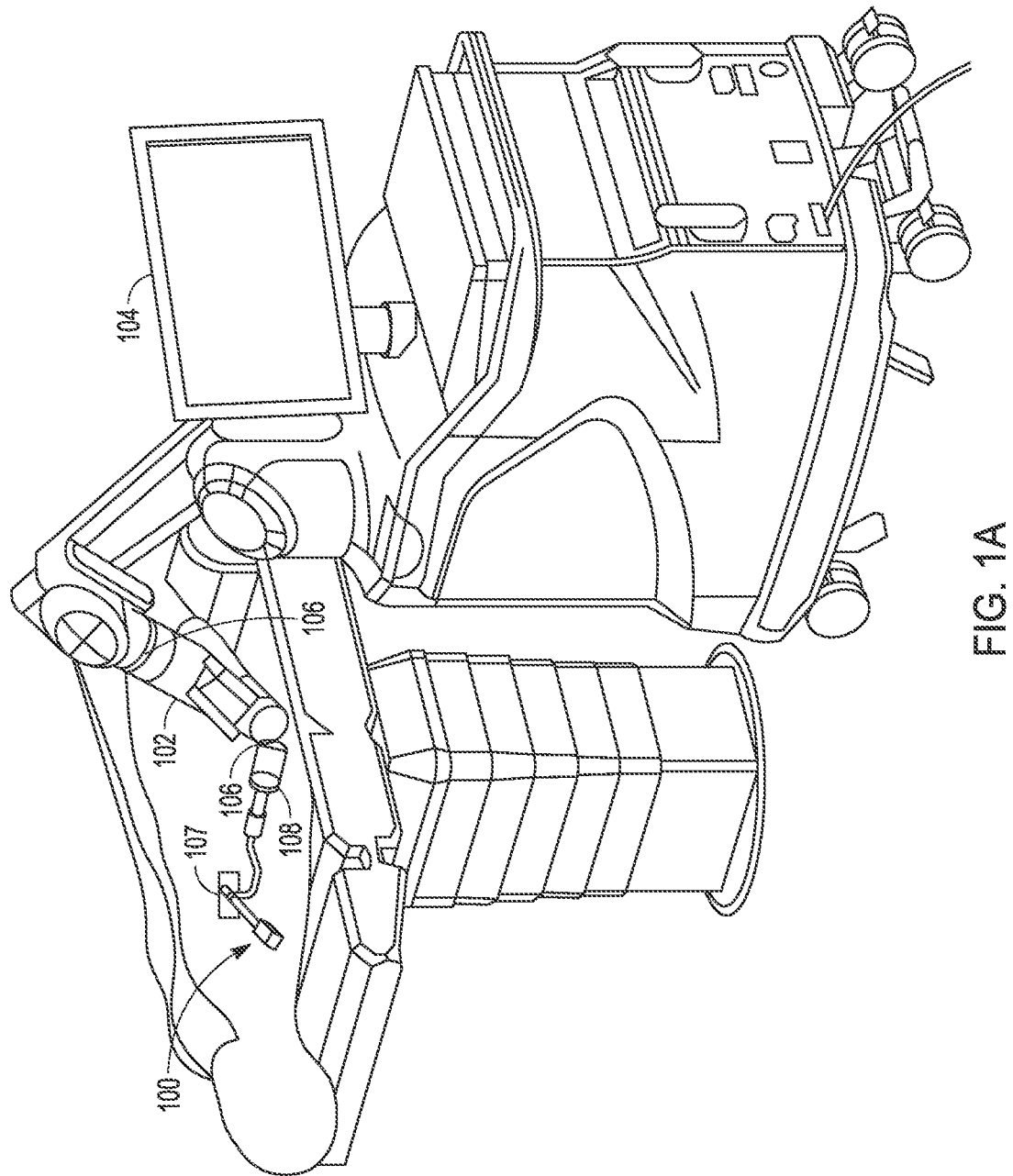
FIG. 1A illustrates an isometric view of an end effector coupled to a robotic arm, in accordance with at least one example of the present application.

The following description and the drawings sufficiently illustrate specific examples to enable those skilled in the art to practice them. Other examples can incorporate structural, process, or other changes. Portions and features of some examples can be included in, or substituted for, those of other examples. Examples set forth in the claims encompass all available equivalents of those claims.

A shoulder joint replacement procedure, or shoulder arthroplasty, can involve making an access incision in a shoulder region of a patient. A guide pin can then be inserted through the incision to contact a bone surface; and is then fixedly coupled to the bone surface of the patient. The guide pin can be used to guide reamers or other cutting instruments to a glenoid surface. Typically, cutting instruments used in shoulder arthroplasty include a rotatable cutting head that is used to cut and shape the humerus, and the glenoid surface, to receive an implant.

Traditional reamers or other rotary cutting instruments often also include a driveshaft operable to rotate the cutting head. The cutting head and the driveshaft generally rotate around a shared axis of rotation. The driveshaft can block a surgeon's view of the cutting head from a position directly above the cutting head. This can require the surgeon to view the targeted bone surface and the cutting head from a position to the side, or from a position offset from, the cutting instrument. In such a situation, the access incision must be large enough to allow for both the insertion of a guide pin, and also for a clear line of sight to the bone surface, generally adjacent the cutting head. Further, the cutting range of a reamer or cutting instrument can be limited to the area directly around, or adjacent to, the guide pin. If subsequent reaming is to be performed, the guide pin must be first removed and then reattached to bone in another area, further lengthening the surgical procedure and increasing the recovery time of a patient. Additionally, when the reamer is restricted to rotating around the guide pin, the reamer is limited to a single cutting angle or trajectory, because the guide pin attached to bone.

The systems and methods disclosed herein provide solutions to the technical problems identified above by providing for a reamer configured to be used with a robotic arm capable of precisely guiding the reaming of a bone. The reamer and the robotic arm can ream the bone within a less invasive incision, which reduces the length of shoulder replacement procedures and the recovery time of a patient. The end effector can include a reamer that can be guided by a robotic arm. The reamer can include a driveshaft and a cutting head, where the cutting head can be rotatable around a separate and offset axis of rotation relative to the driveshaft.

The robotic arm and the end effector can together eliminate the need for a guide pin. The offset reamer can reduce the size of an access incision by affording a surgeon a view from directly above a cutting head, eliminating the need for viewing a cutting head from the side. The robotic arm can articulate to precisely position the reamer to access a bone surface at a variety of different cutting angles or trajectories, for greater bone preservation. These benefits can together enable a surgeon to complete a shoulder joint replacement procedure using a smaller incision, and with improved accuracy and greater bone preservation, helping to provide improved outcomes for a patient, such as increased repeatability, a shorter hospital stay, and a reduced recovery time.

While the following examples are discussed in view of a shoulder arthroplasty procedure, the described robotic arm, end effector, and reamer can be utilized in other similar arthroplasty procedures. For example, the robot, end effector, and reamer can be utilized to ream an acetabulum during a hip arthroplasty procedure. The offset nature of the reaming, in combination with the robotic arm, can provide similar benefits in a hip arthroplasty procedure as described throughout for the shoulder arthroplasty.

Figure 1B:
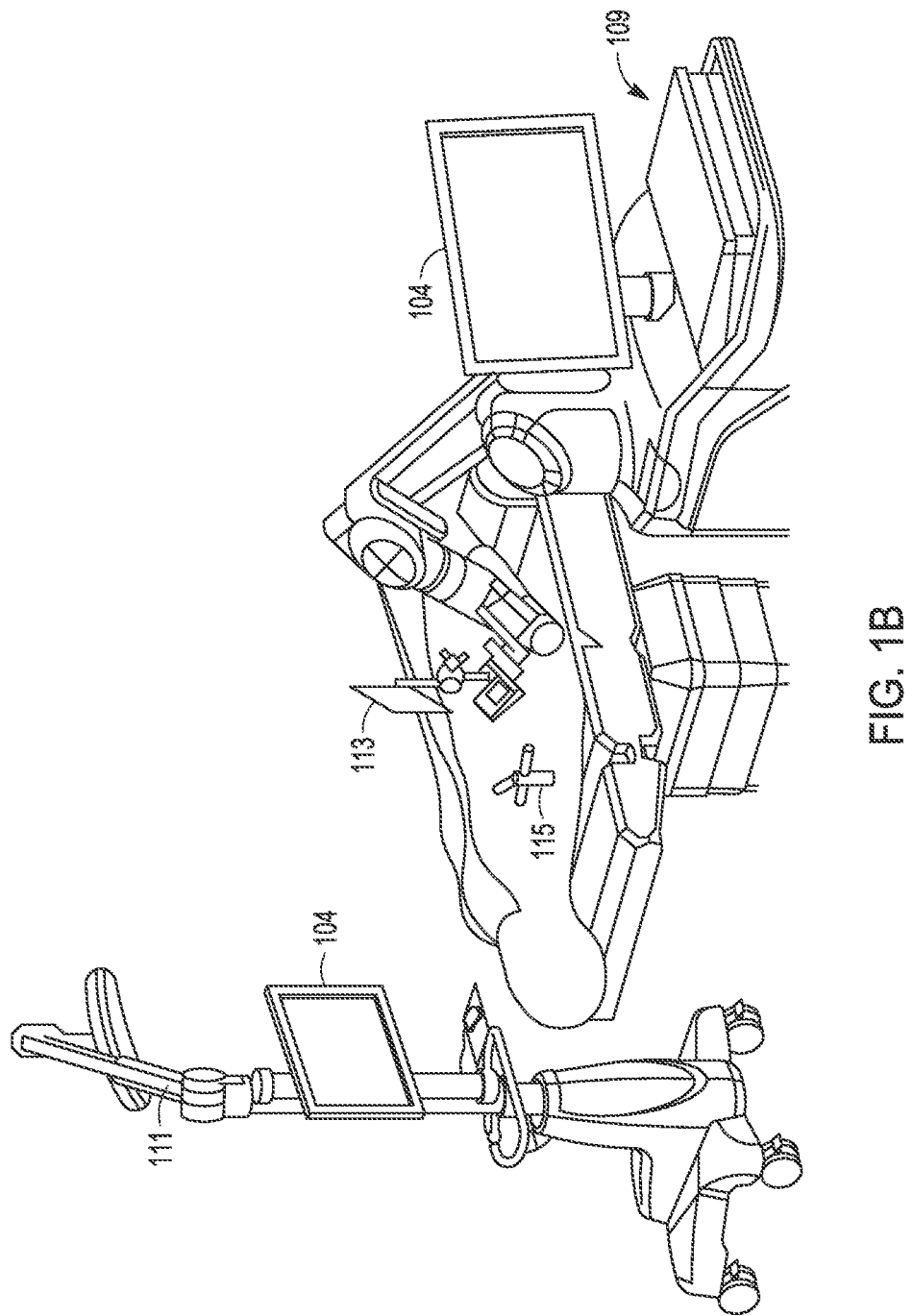
FIG. 1B illustrates an isometric view of a robotic arm, in accordance with at least one example of the present application.
Figure 1C:
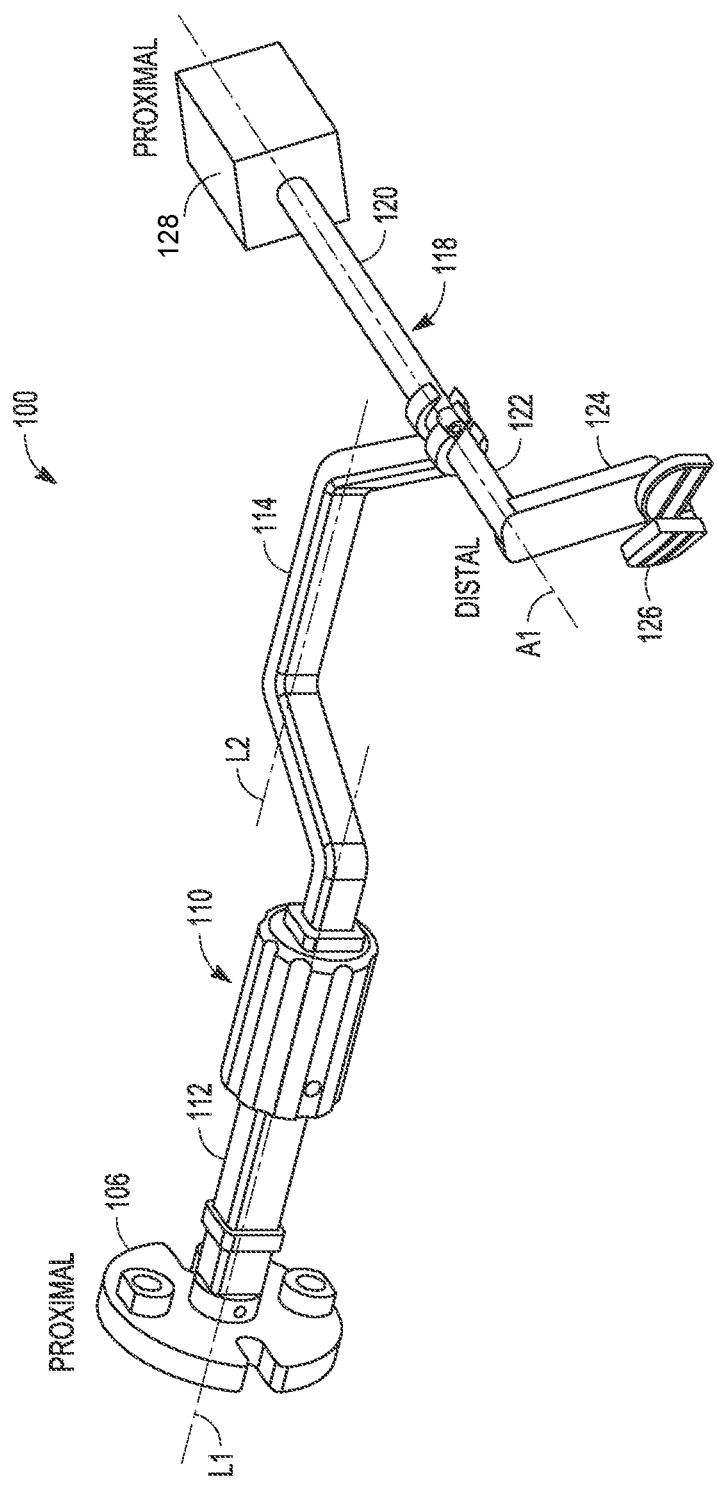
FIG. 1C illustrates an isometric view of an end effector, in accordance with at least one example of the present application.

FIG. 1A illustrates an isometric view of an end effector 100 coupled to a robotic arm 102, in accordance with at least one example of the present application. FIG. 1B illustrates an isometric view of a robotic arm 102, in accordance with at least one example of the present application. FIG. 1C illustrates an isometric view of the end effector 100, in accordance with at least one example of the present application. Also shown in FIG. 1C are a longitudinal axis L1, longitudinal axis L2, a first axis A1, and orientation indicators Proximal and Distal. FIGS. 1A-1C are discussed below concurrently. The end effector 100 can be coupled to the robotic arm 102. Robotic arm 120 can be a 6 degree-of-freedom (DOF) robot arm, such as the ROSA® robot from Medtech, a Zimmer Biomet Holdings, Inc. company.

The robotic arm 102 can be controlled by a surgeon with various control devices or systems. For example, a surgeon can use a control system (e.g., a controller that is processor-implemented based on machine-readable instructions, which when implemented cause the robotic arm to move automatically or to provide force assistance to surgeon-guided movement) to guide the robotic arm 102. A surgeon can use anatomical imaging, such as displayed on a display screen 104, to guide and position the robotic arm 102. Anatomical imaging can be provided to the display screen 104 with various imaging sources, such as one or more cameras positioned on the end effector 100, or intraoperative fluoroscopy, such as a C-arm. The robotic arm 102 can include two or more articulating joints 106 capable of pivoting, rotating, or both, to provide a surgeon with wide range of adjustment options.

The anatomical imaging, for example, can be imaging of internal patient anatomy within an incision 107. The incision 107 can be made in a variety of positions on a patient. For example, in a shoulder arthroplasty procedure, the incision 107 can be made in a shoulder region of a patient. The incision 107 can be configured to allow the end effector 100, coupled to the robotic arm 102, to access a bone surface, or other anatomy of the patient. The end effector 100 can also include a base 108, which can be configured to couple the end effector 100 to the robotic arm 102. The end effector 100 can also include a retainer 110.

As shown in FIG. 1B, the robotic arm 102 can include a computing system 109, which can also communicate with display screens 104 and a tracking system 111. The tracking system 111 can be operated by the computing system 109 as a stand-alone unit. The computing system 109 can utilize the Polaris optical tracking system from Northern Digital, Inc. of Waterloo, Ontario, Canada. Additionally, the tracking system 111 can comprise the tracking system shown and described in Pub. No. US 2017/0312035, titled "Surgical System Having Assisted Navigation" to Brian M. May, which is hereby incorporated by this reference in its entirety.

The tracking system 111 can monitor a plurality of tracking elements, such as tracking elements 113 and 115. The tracking elements 113 and 115 can be affixed to objects of interest, to track locations of multiple objects within a surgical field.

The tracking system 111 can function to create a virtual three-dimensional coordinate system within the surgical field for tracking patient anatomy, surgical instruments, or portions of the end effector 100 or the robotic arm 102. One or more of the tracking elements 113 and 115 can be tracking frames including multiple IR reflective tracking spheres, or similar optically tracked marker devices. In an example, one or more of the tracking elements 113 and 115 can be placed on or adjacent one or more bones of patient. In other examples, one or more of the tracking elements 113 and 115 can be placed on the end effector 100 or an implant to accurately track positions within the virtual coordinate system. In each instance, the tracking elements 113 and 115 can provide position data, such as a patient position, a bone position, a joint position, an implant position, a position of the robotic arm 102, or the like.

As shown in FIG. 1C, the retainer 110 of the end effector 100 can be comprised of a bar 112 and an arm 114. The bar 112 and the arm 114 can generally be shafts having a square cross-sectional shape, but can also be shaped as round, rectangular, or the like. The retainer 110 can be solid or hollow. The bar 112 can extend along the longitudinal axis L1. The arm 114 can have portions which extend along the longitudinal axis L2. The arm 114 can have portions which extend at tangents to (or are not parallel with) the longitudinal axis L1; or can have portions which extend perpendicular to the longitudinal axis L1. For example, the arm 114 can have portions which extend along longitudinal axis L2. Longitudinal axis L2 can be parallel with, but laterally offset from, longitudinal axis L1. The first axis A1 can be perpendicular to the longitudinal axis L1, or L2. The arm 114 of the retainer 110 can be C-shaped, U-shaped, V-shaped, or a variety of other shapes.

The end effector 100 can include a reamer 116, which can be configured to cut and shape a bone surface of a patient. The reamer 116 can include a primary housing 118. The primary housing 118 can include a proximal portion 120 and a distal portion 122. The primary housing 118 can be generally cylindrical in shape; but can also comprise other three-dimensional shapes such as rectangular prisms. The primary housing 118 can be coupled to the arm 114 of the retainer 110; to couple the reamer 116 to the retainer 110. The primary housing 118 can extend along the first axis A1. The reamer 116 can include a secondary housing 124 that can be generally cylindrical in shape; but can also comprise other three-dimensional shapes. The secondary housing 124 can extend orthogonally to the first axis A1; but can extend in other non-parallel orientations with respect to the first axis A1.

The reamer 116 can include a cutting head 126. The cutting head 126 can be a rotary cutting head configured to cut and shape bone via rotation. The cutting head 126 can be rotatably coupled to the secondary housing 124. As a result, the cutting head 126 can be vertically or laterally offset from the first axis A1 and the primary housing 118. The end effector 100 can include a motive source 128 that can be coupled to the proximal portion 120 of the primary housing 118. The motive source 128 can be an electrically actuated motor, a pneumatically operated motor, or other types of rotating drive sources. The motive source 128 can provide rotational drive to the cutting head 126 through the primary housing 118 and the secondary housing 124.

In the operation of some examples, the end effector 100 can be coupled to a robotic arm 102 in preparation for a surgical procedure. The surgical procedure can be a shoulder arthroplasty; but can also be other types of joint replacement procedures. A surgeon can make an incision 107 in a shoulder region of a patient. The robotic arm 102 can guide and position the end effector 100 to, and within, the incision 107. The cutting head 126, and other portions of the reamer 116, can be guided to a bone surface of a patient using the robotic arm 102 in a cooperatively-controlled mode utilizing robotic guidance. The motive source 128 can be selectively controlled to rotate the cutting head 126. The cutting head 126 can thereby be used to ream a bone surface of the patient, to shape the bone surface to receive an implant. In contrast to traditional methods using a fixed guide pin, the positioning of the end effector 100, including the cutting angle or trajectory of the reamer 116, can be easily adjusted intra-procedurally with the robotic arm 102.

The robotic arm 102 can provide a number of benefits to a patient. The end effector 100, with the robotic arm 102, can eliminate the need for a fixed guide pin in joint replacement procedures. The ability of the robotic arm 102 to be adjustably pivoted, rotated, or otherwise articulated intra-procedurally, either autonomously or cooperatively with the operator, to adjust the cutting angle or trajectory of the reamer 116 can allow for greater bone preservation than would be possible with a fixed guide pin. The robotic arm 102 can control the position, movement, and force applied by the cutting head 126 of the reamer 166 more precisely and steadily than a human hand, such that the cutting head 126 does not require a depth stop to prevent over-penetration of the cutting head 126 into a bone surface. This can reduce the cost of producing the reamer 116, and further decrease the amount of space needed within an incision for a cutting instrument to operate.

The cutting head 126 of the reamer 116 can be rotatable around a separate and offset axis of rotation relative to the motive source 128. The offset of the cutting head 126 can reduce the size of an access incision by affording a surgeon a view from directly above a cutting head, eliminating the need for viewing a cutting head from the side. These benefits can enable a surgeon to complete a shoulder joint replacement procedure with improved accuracy and greater bone preservation; and provide a patient with shorter hospital stay and a reduced recovery time.

Figure 2:
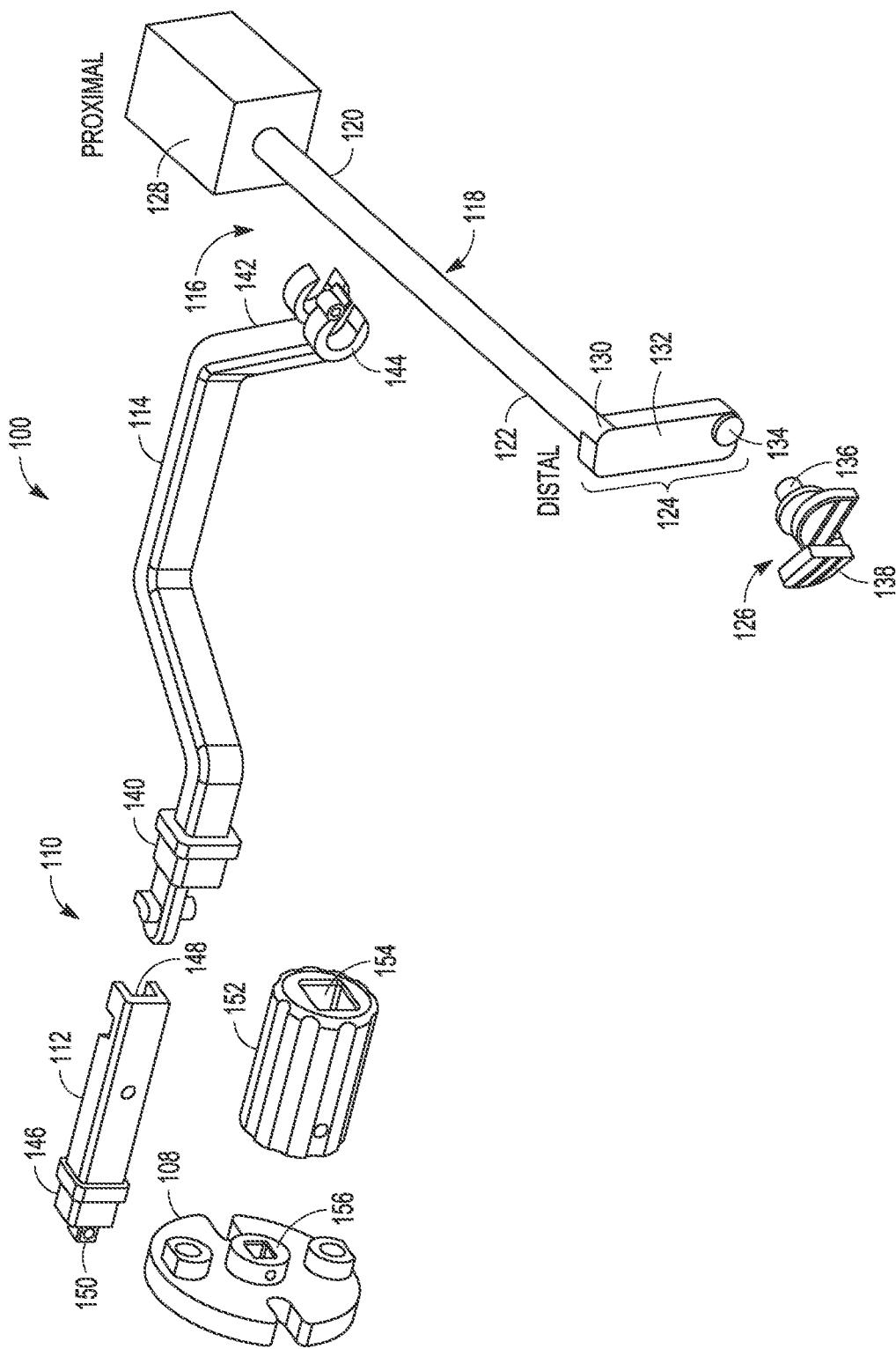
FIG. 2 illustrates an exploded view of an end effector, in accordance with at least one example of the present application.

FIG. 2 illustrates an exploded view of an end effector 100, in accordance with at least one example of the present application. Also shown in FIG. 2 are orientation indicators Proximal and Distal relating to relative positions along the reamer 116. As shown in FIG. 2, the secondary housing 124 can include a first portion 130 and a second portion 132 defining a bore 134. The cutting head 126 can include a connector 136 and a cutting portion 138. The arm 114 of the retainer 110 can include a proximal link 140, a distal end 142, and a coupler 144. The bar 112 of the retainer 110 can include a proximal end 146, a distal link 148, and an extension 150. The end effector 100 can also include a collar 152 and a channel 154.

The first portion 130 and the second portion 132 can be generally opposite portions of the secondary housing 124 of the reamer 116. The first portion 130 can be coupled to the distal portion 122 of the primary housing 118. The second portion 132 can include the bore 134. The cutting portion 138 can include cutting teeth, or other cutting or abrasive features. The cutting head 126 can form a generally cylindrical shape; but can also form other three-dimensional shapes. The connector can be configured to extend into, and engage the bore 134 of the secondary housing 124, to couple the cutting head 126 to the reamer 116.

The proximal link 140 and the distal end 142 can be generally opposite proximal and distal portions of the arm 114. The arm 114 can include a coupler 144. The coupler 144 can be positioned on, or can extend distally from, the distal end 142 of the arm 114. The coupler 144 can be configured to releasably engage the primary housing 118, to selectively couple the reamer 116 to the retainer 110 such that the primary housing 118 can be connected by the distal end 142 of the arm 114. The coupler 144 can engage the primary housing 118.

The distal link 148 of the bar 112 can be coupled to the proximal link 140 of the arm 114. The retainer 110 can include the collar 152. The collar 152 can be generally cylindrical in shape. The collar 152 can be configured to further secure the bar 112 to the arm 114. The collar 152 can include the channel 154 that can be configured to accept, conform to, or encompass at least a portion of both the proximal link 140 and the distal link 148. The collar 152 can thereby aid in coupling the bar 112 to the arm 114, by encompassing portions of the proximal link 140 and the distal link 148.

The bar 112 of the retainer 110 can include the extension 150. The extension 150 can be a protrusion extending proximally from the proximal end 146. The protrusion can be generally rectangular, cuboid, or cylindrical in shape, but can also comprise other three-dimensional shapes. The base 108 can include a bore 156. The bore 156 can be configured to accept and engage the extension 150 to couple the retainer 110 to the base 108. As the base 108 is configured to engage with a distal end of a robotic arm, such as the robotic arm 102 shown in FIG. 1A, the base 108 can couple the retainer 110 and the reamer 116 to a robotic arm.

Figure 3:
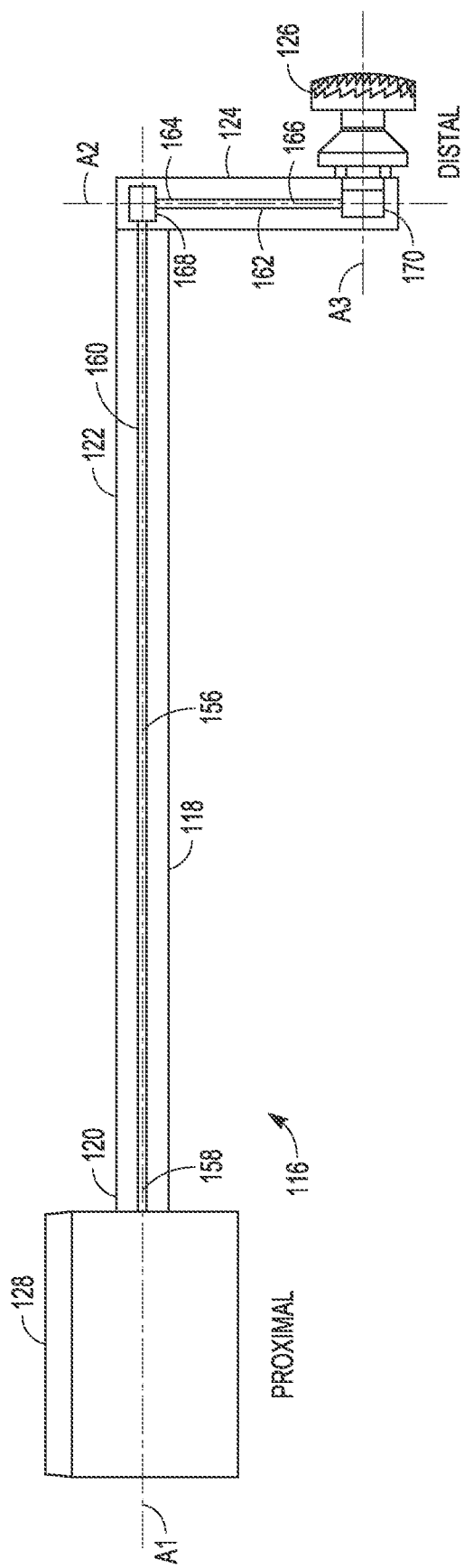
FIG. 3 illustrates a side isometric view of a reamer, in accordance with at least one example of the present application.

FIG. 3 illustrates a side isometric view of a reamer 116, in accordance with at least one example of the present application. Also shown in FIG. 3 is the first axis A1, a second axis A2, a third axis A3, and orientation indicators Proximal and Distal. As shown in FIG. 3, the reamer 116 can include a primary driveshaft 156, (including a proximal shaft portion 158 and a distal shaft portion 160), a secondary driveshaft 162, a medial secondary portion 164, a lateral secondary portion 166, a first joint 168, and a second joint 170.

The primary driveshaft 156 can extend longitudinally along, and rotate around, the first axis A1. The primary driveshaft 156 can be configured to extend within the primary housing 118. The proximal portion 158 of the primary driveshaft 156 can be coupled to the motive source 128. The motive source 128 can thereby rotate the primary driveshaft 156 around the first axis A1 to rotate the primary driveshaft 156.

The secondary housing 124 can extend along the second axis A2. The second axis A2 can be orthogonal to the first axis A1. In other examples, the second axis A2 can be not parallel with the first axis A1. The reamer 116 can include the secondary driveshaft 162. The secondary driveshaft 162 can extend along, and rotate around, the second axis A2. The secondary driveshaft 162 can be configured to extend within the secondary housing 124, such that the secondary housing 124 can encompass the secondary driveshaft 162.

The reamer 116 can also include the first joint 168 and the second joint 170. The first joint 168 and the second joint 170 can be, for example, universal joints, but can also comprise a variety of other types of flexible joints or couplers. The first joint 168 can couple the distal portion 160 of the primary driveshaft 156 to the medial secondary portion 164 of the secondary driveshaft 162. The second joint 170 can couple the lateral secondary portion 166 of the secondary driveshaft 162 to a connector of the cutting head 126. The primary driveshaft 156 and the secondary driveshaft 162 can thereby rotatably couple the motive source 128 to the cutting head 126 while extending within the primary housing 118 and the secondary housing 124. The cutting head 126 can extend along, and rotate around, the third axis A3. The third axis A3 can extend parallel to, but laterally offset from, the first axis A1. In other examples, the third axis A3 can be in other non-parallel orientations with respect to the first axis A1. As the primary driveshaft 156 is offset away from the cutting head 126, a surgeon can view the cutting head 126 from a position directly above the cutting head 126. This can provide the benefits of a smaller access incision and a less invasive procedure with a shorter recovery time for a patient.

Figure 4:
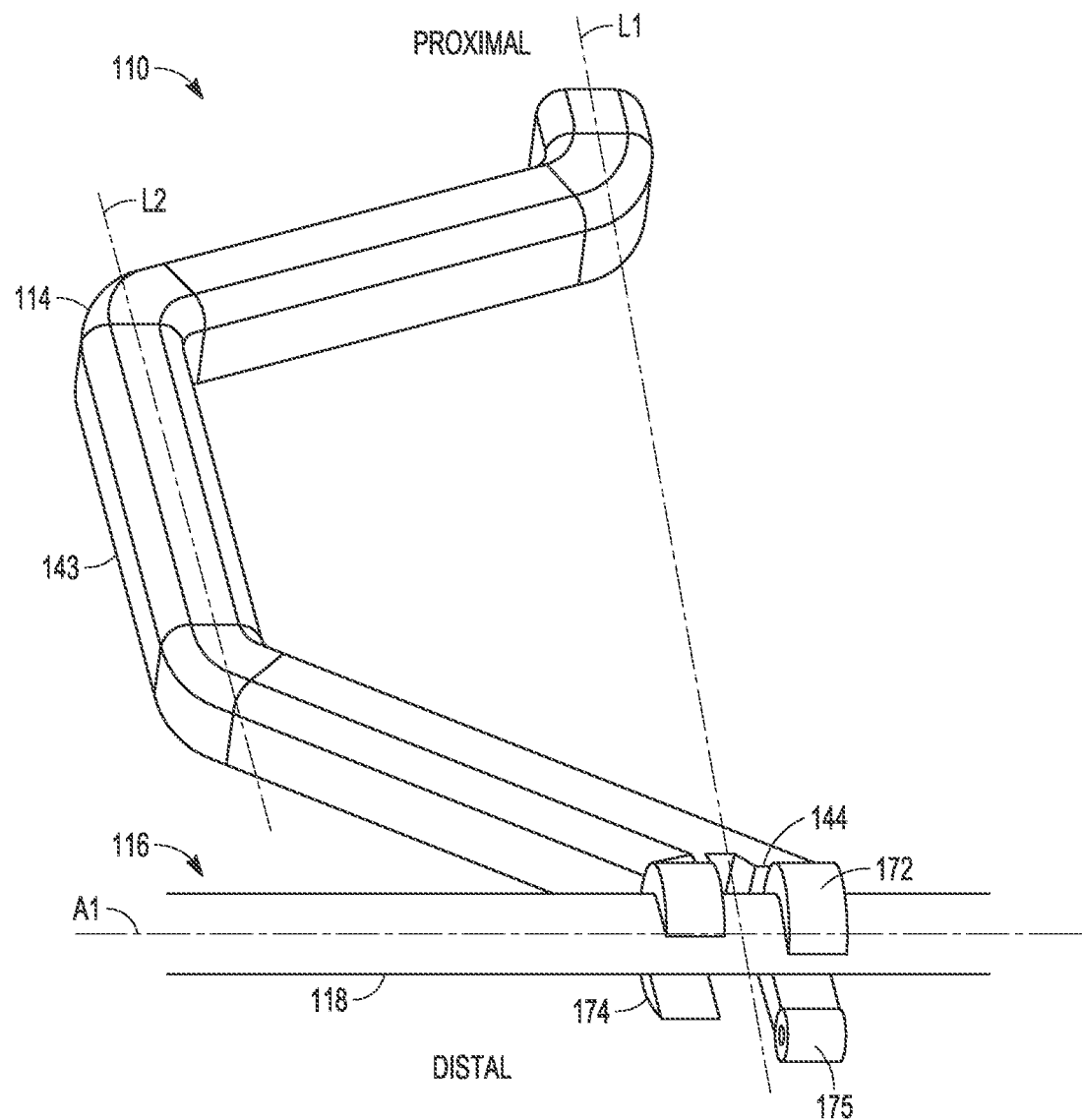
FIG. 4 illustrates an isometric view of a retainer, in accordance with at least one example of the present application.

FIG. 4 illustrates an isometric view of a retainer 110, in accordance with at least one example of the present application. Also shown in FIG. 4 is a longitudinal axis L1, a longitudinal axis L2, a first axis A1, and orientation indicators Proximal and Distal. As shown in FIG. 4, the arm 114 can include an offset segment 143. The offset segment 143 can extend along the longitudinal axis L2. Longitudinal axis L2 can be parallel with, but laterally offset from, longitudinal axis L1. The lateral offset of the offset segment 143 can allow the arm 114 of the retainer 110 to extend around various external anatomical features of a patient, in order to provide greater working space and positioning options for a surgeon, when using the end effector 100. Other portions of the arm 114, between the offset segment 143 and the proximal can extend at a tangent between the longitudinal axes L1 and L2. The arm 114 of the retainer 110 can thereby be C-shaped, U-shaped, V-shaped, or a variety of other shapes.

The arm 114 of the retainer 110 can include the coupler 144, which can be configured to couple the retainer 110 to the reamer 116. The coupler 144 can include a first connector 172 and a second connector 174. The first portion 172 and the second connector 174 can each be generally C-shaped couplers, but each can also form other three-dimensional shapes. The first connector 172 and the second connector 174 can extend distally from the distal portion 144, along the longitudinal axis L1. The first connector 172 and the second connector 174 extend from the distal end 142 in a parallel orientation relative to each other. The coupler 144 can also include a protrusion 175. The protrusion 175 can be generally cylindrically-shaped but can also comprise other three-dimensional shapes. The protrusion 175 can extend distally from one, or both, of the first connector 172 and the second connector 174.

The protrusion 175 can be configured to engage the primary housing 118 of the reamer 116, to further aid in securely retaining the primary housing 118 within the coupler 144. The coupler 144, including the protrusion 175, can be configured to fixedly, or adjustably, couple the arm 114 to the primary housing 118. For example, the coupler 144 can be configured to allow the primary housing 118 to slide proximally and distally along the first axis A1, within the coupler 144. Alternatively, the coupler 144 can be configured to fixedly retain the primary housing 118 in certain situations, for example, when it is desirable to apply an increased force to the cutting head 126.

Figure 5A:
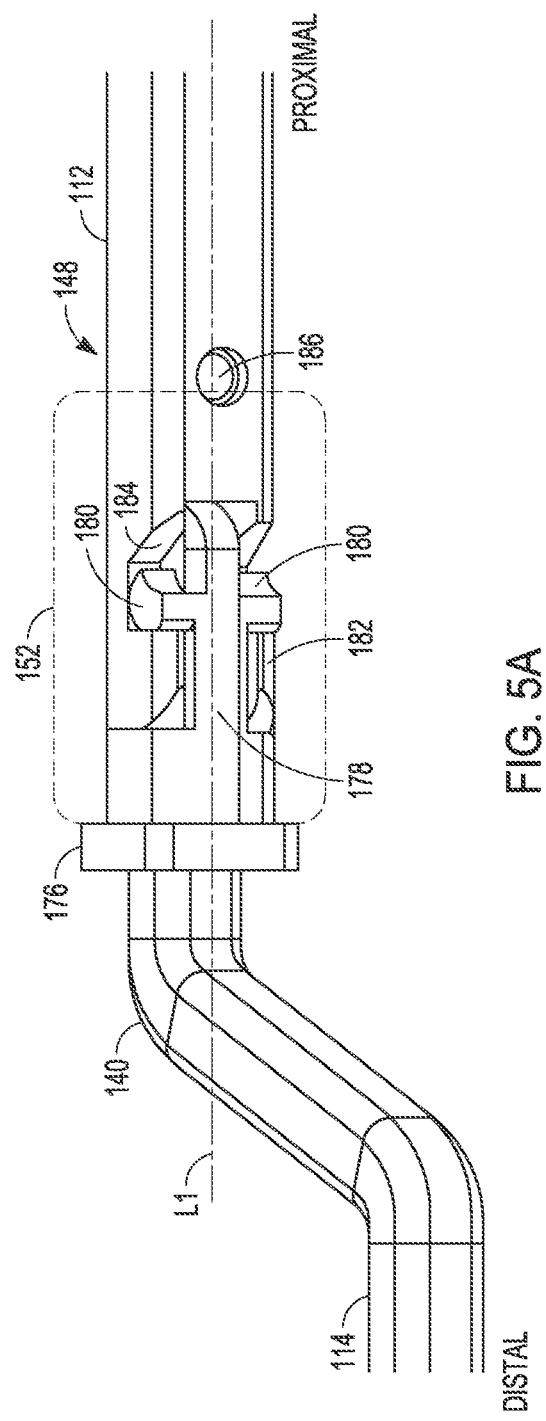
FIGS. 5A-5B illustrate side isometric views of a retainer and a collar, in accordance with at least one example of the present application.
Figure 5B:
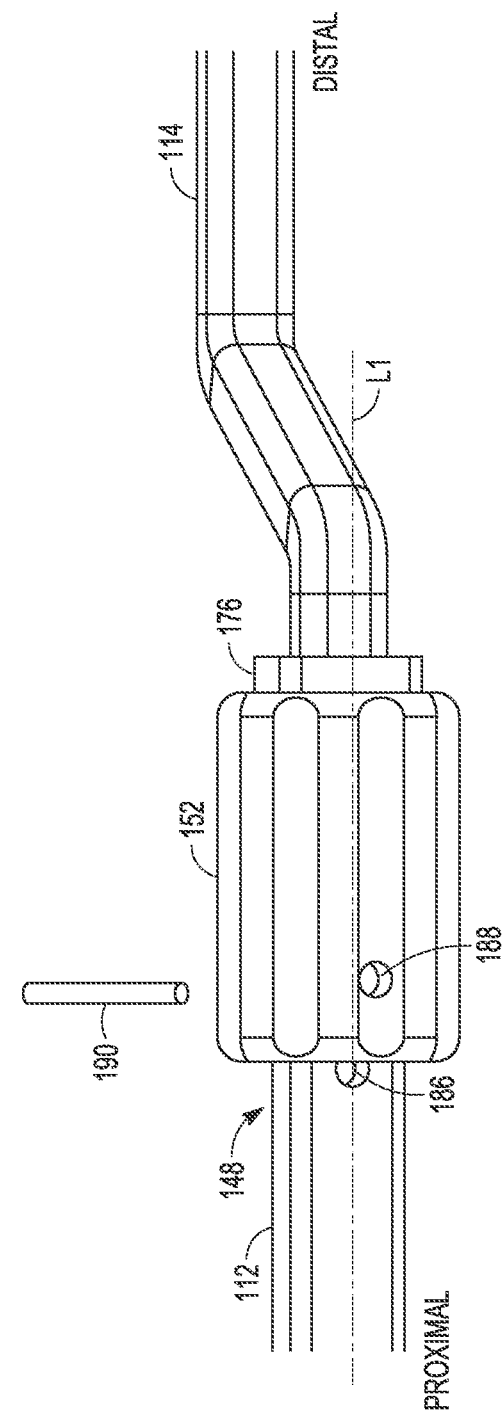

FIGS. 5A-5B illustrate side isometric views of a retainer 110 and a collar 152, in accordance with at least one example of the present application. In FIG. 5A, the collar 152 is shown in phantom. Also shown in FIGS. 5A-5B are a longitudinal axis L1, and orientation indicators Proximal and Distal. FIGS. 5A and 5B are discussed below concurrently.

As shown in FIGS. 5A-5B, the arm 114 of the retainer 110 can include a flange 176. The flange 176 can be protrusion extending outwardly from the proximal link 140 of the arm 114. The flange 176 can be generally cuboid in shape, but can also be rectangular or other three-dimensional shapes. The flange 176 can extend vertically and laterally (e.g., radially) beyond a height and a width of the arm 114. The flange 176 can be configured to limit distal travel of the collar 152, such as when the collar 152 is positioned over at least a portion of the proximal link 140 of the arm 114.

The proximal link 140 of the arm 114 can include a body 178 and arms 180. The body 178 can be a portion of the proximal link 140 having a reduced height and width, relative to dimensions of other portions of the arm 114. The body 178 can extend along the longitudinal axis L1. The body 178 can generally be a shaft having a rectangular shape, or the like, but the body 178 can also form other three-dimensional shapes. The arms 180 can be protrusions or extensions extending orthogonally from the body 178. The arms 180 can generally be a shaft having a cylindrical shape, but the arms 180 can also form other three-dimensional shapes.

The distal link 148 of the bar 112 can include a channel 182 and a recess 184. The channel 182 can generally extend along, and through a distal end, of the distal link 148. The channel 182 can extend within the distal link 148 along the longitudinal axis L1. The channel 182 can be configured to accept, contact, and retain the body 178 of the proximal link 140. The recess 184 can extend within the distal link 148 orthogonally to the longitudinal axis L1. The recess 184 can be configured to accept, contact, and retain the arms 182 of the proximal coupler 178.

As shown in FIG. 5B, the distal link 148 of the bar 112 can also include a first lock bore 186. The lock bore 186 can extend transversely within the distal link 148; orthogonally to the longitudinal axis A1. The collar 152 can include a first pin bore 188. The first pin bore 188 can extend transversely within the collar 152; orthogonally to the longitudinal axis A1. The first lock bore 186 and the first pin bore 188 can each be configured to accept, contact, and retain a first pin 190. The first pin 190 can be a solid pin, a roll pin, or other types of generally cylindrical fasteners.

In the operation of at least one example, the collar 152 can be positioned around the first portion 112. The distal link 148 of the bar 112 can engage the proximal link 140 of the arm 114, to couple the bar 112 to the arm 114. The collar 152 can slide distally over and along the bar 112 until the collar 152 contacts the flange 176, such the first lock bore 186 is aligned with the first pin bore 188. When the collar 152 contacts the flange 176, the collar 152 can be in a position encompassing both the proximal link 140 of the arm 114 and the distal link 148 of the bar 112, furthering securing the bar 112 to the arm 114 by helping to limit relative lateral or radial movement of the proximal coupler 178 and the distal link 148, helping to prevent the proximal coupler 178 from disengaging the distal link 148. The first pin 190 can be inserted through the first pin bore 188 in the collar 152 and through the first lock bore 186 in the distal link 148 to lock the collar 152 in position, which can help prevent the collar 152 from traveling proximally along the longitudinal axis A1.

Figure 6:
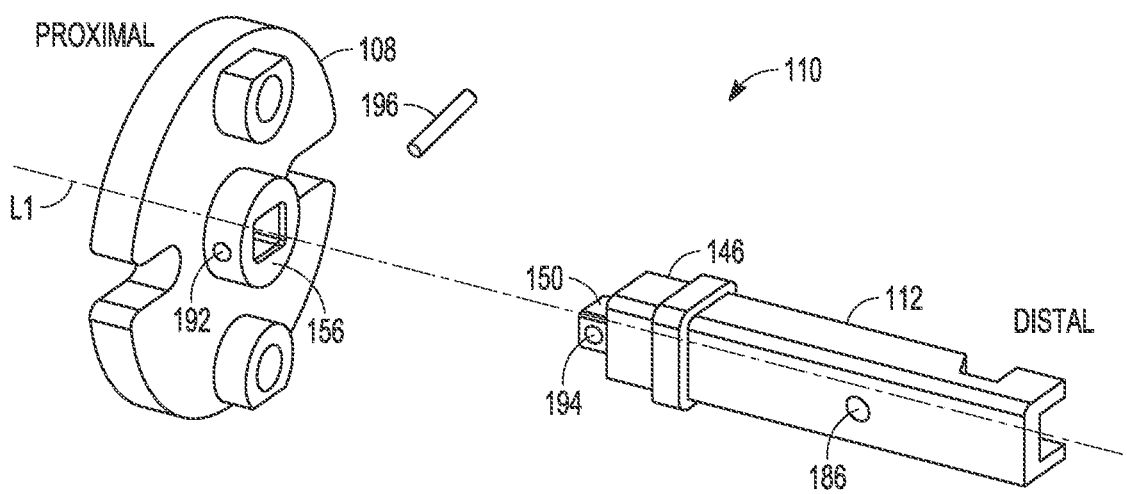
FIG. 6 illustrates an isometric view of a retainer coupled to reamer, in accordance with at least one example of the present application.

FIG. 6 illustrates an isometric view of a retainer 110 and a base 108 of an end effector 100, in accordance with at least one example of the present application. Also shown in FIG.

6 is a longitudinal axis L1, and orientation indicators Proximal and Distal. As shown in FIG. 6, the base 108 can include a second lock bore 192. The second lock bore 192 can extend within the base 108, orthogonally to the longitudinal axis L1. The extension 150, which can extend from the proximal end 146 of the bar 112, can include a second pin bore 194. The second pin bore 194 can extend within the extension 150; orthogonally to the longitudinal axis L1. The second lock bore 192 and the second pin bore 194 can each be configured to accept, contact, and retain a second pin 196. The second pin 196 can be a solid pin, a roll pin, or other types of generally cylindrical fasteners.

In the operation of at least one example, the extension 150 of the bar 112 can be inserted into the bore 156 of the base 108, such that the second lock bore 192 is aligned with the second pin bore 194. The second pin 196 can then be inserted into the second lock bore 192 of the base 108 and the second pin bore 194 in the extension 150 to couple the bar 112 to the base 108. As the base 108 is configured to engage with a distal end of a robotic arm, such as the robotic arm 102 shown in FIG. 1A, the base 108 can thereby couple the bar 112 to the robotic arm 102.

The base 108, the retainer 110, the primary housing 118, the secondary housing 124, the collar 152, the primary driveshaft 156, the secondary driveshaft 162, the first joint 170, the second joint 172, and the first 190 and the second 196 pins, can each be made from, in an example, plastics or composites. For example, the components listed above can be molded, or otherwise made from, ABS plastic. The base 108, the retainer 110, the primary housing 118, the secondary housing 124, the lock collar 152, the primary driveshaft 156, the secondary driveshaft 162, the first joint 170, the second joint 172, and the first 190 and the second 196 pins, can also each be made from stainless steel, or other metals via machining or metallic molding.

Figure 7:
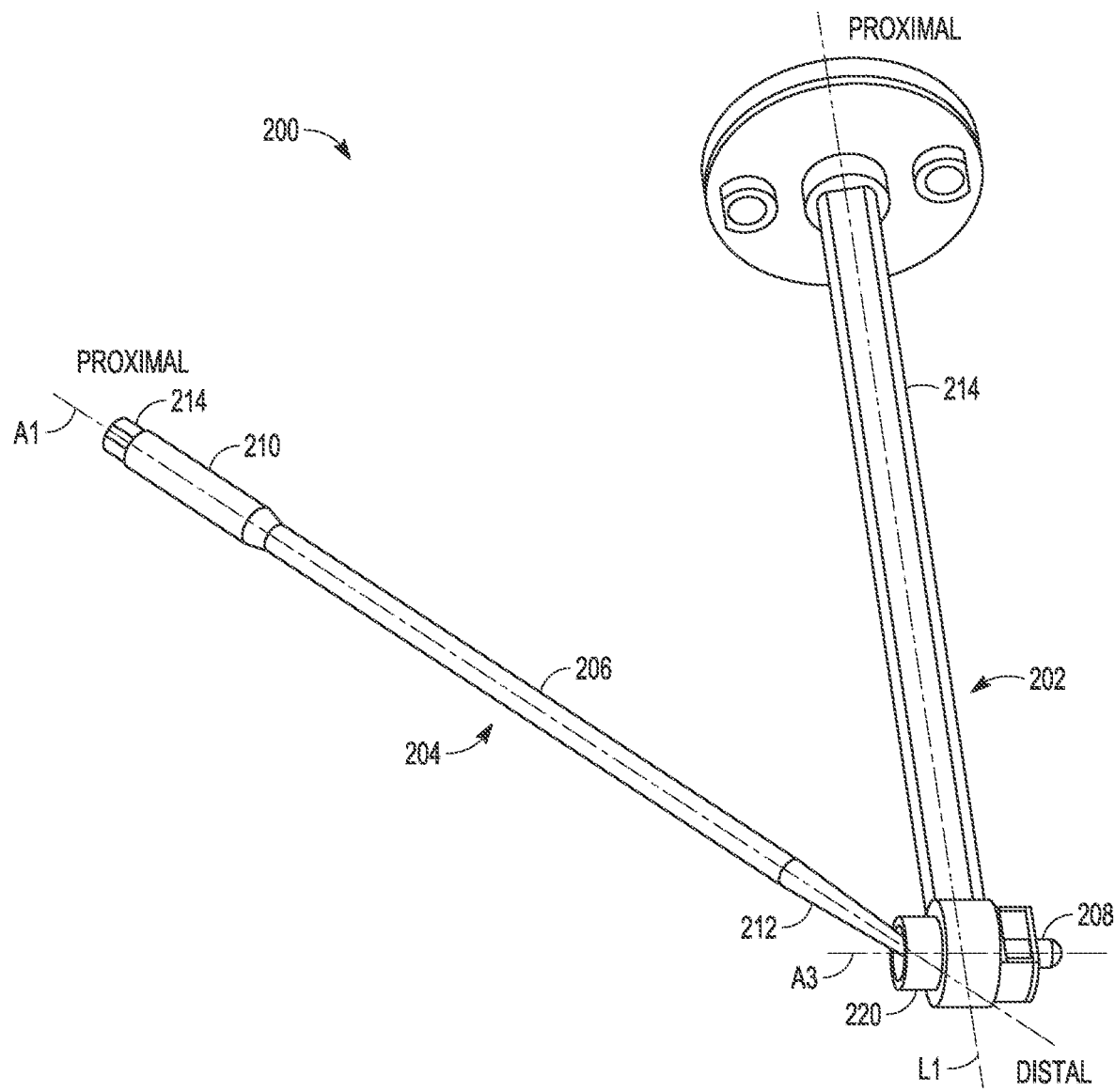
FIG. 7 illustrates an isometric view of an end effector, in accordance with at least one example of the present application
Figure 8:
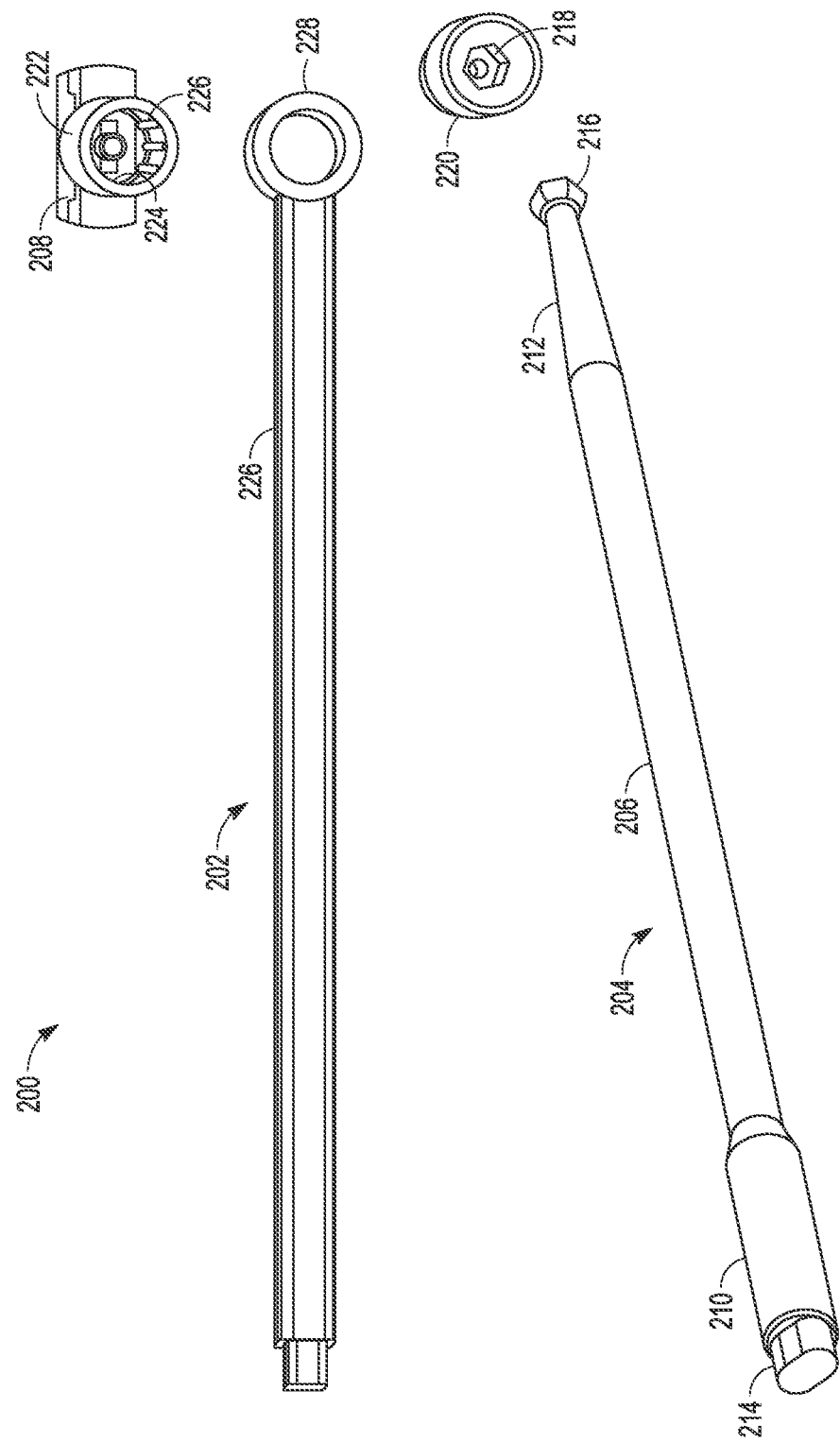
FIG. 8 illustrates an exploded view of an end effector, in accordance with at least one example of the present application.

FIG. 7 illustrates an isometric view of an end effector 200, in accordance with at least one example of the present application. FIG. 8 illustrates an exploded view of an end effector 200, in accordance with at least one example of the present application. Also shown in FIG. 7 is a first axis A1, a third axis A3, a longitudinal axis L1, and orientation indicators Proximal and Distal. FIGS. 7-8 are discussed below concurrently. The end effector 200 can include any of the components of the end effector 100 discussed and shown with regard to FIGS. 1A-6 above.

The end effector 200 can include a retainer 202 extending along the longitudinal axis L1. The retainer 202 can be similar to the retainer 114, such as including the proximal link 140 or the offset segment 143; and can be configured to engage with the bar 112, or with the base 108 directly. The end effector 200 can include a reamer 204. The reamer 204 can be similar to the reamer 116, such as including the primary 118 and the secondary 162 driveshafts extending along the first axis A1 and along the second axis A2, respectively, to enable the third axis A3 of the cutting head 126 to be laterally offset from the first axis A1 of the primary driveshaft 118. In some examples, such as the end effector 200 shown in FIGS. 7-8, the reamer 204 can enable the orientation of the first axis A1 to change relative to the orientation of the third axis A3. For example, a primary driveshaft 206 defining the first axis A1 can be adjustable relative to a cutting head 208 defining the third axis A3. The primary driveshaft 206 can include a proximal shaft portion 210 and distal shaft portion 212. The proximal shaft portion 210 can include a protrusion 214. The protrusion 214 can be configured to engage with a drive source, such as the motive source 128.

The distal shaft portion 212 can include a driver 216. The driver 216 can be a feature formed on, or coupled to, the distal portion 212. The driver 216 can generally be in the shape of a hexagonal or an octagonal prism; but can also form other three-dimensional shapes. The reamer can include a drive coupler 220. The driver 216 can be configured to engage, such as by being positioned at least partially within, a head 218 of the drive coupler 220. The head 218 can be a complimentary recess, relative to the shape of the driver 216, formed in the drive coupler 220. The drive coupler 220 can be coupled to the cutting head 208, such via the coupler 136 shown in FIG. 2. The drive coupler 220 can thereby engage both the cutting head 208 and the driver 216 to transfer rotational motion from driveshaft 206 to the cutting head 208. The driver 216 can securely engage the head 218 at a variety of angles relative to the drive coupler 220, to thereby allow angulation of the primary driveshaft 206 relative to the cutting head 208.

The reamer 204 can include a bushing 222. The bushing 222 can generally be cylindrical in shape; and can include a bore 224. The bore 224 can be configured to accept the drive coupler 220, such to allow the drive coupler 220 to rotate within the bore 224 of the bushing 222. The reamer 204 can further include a plurality of bearings 226. The bearings 226 can be, for example, ball or needle bearings located within the bore 224. The bearings 226 can be located between an outer surface of the drive coupler 220 and an inner surface of the bushing 222 defining the bore 224. As such, the bushing 222 can function as an outer bearing race and the drive coupler 220 can function as an inner bearing race. The bearings 226 could also be a bushing or could include surfaces to promote articulation or rotation. The bearings 226 can thereby reduce friction between the bushing 222 and the drive coupler 220.

The retainer 202 can include distal portion 226. The distal portion 226 can include or otherwise form a housing 228. The housing 228 can generally be cylinder in shape; and can be configured to encompass and fixedly retain the bushing 222. The end effector 200 can thereby enable the primary driveshaft 206 to be adjusted and angled relative to the cutting head 208, independently of, or in addition to, the lateral offset between the first axis A1 and the third axis A3 shown in FIG. 3 above. This can enable a user to intra-procedurally adjust the orientation of the primary driveshaft, such as to improve the visibility of a target bone surface for a surgeon by moving the driveshaft out of the surgeon's line of sight.

Figure 9:
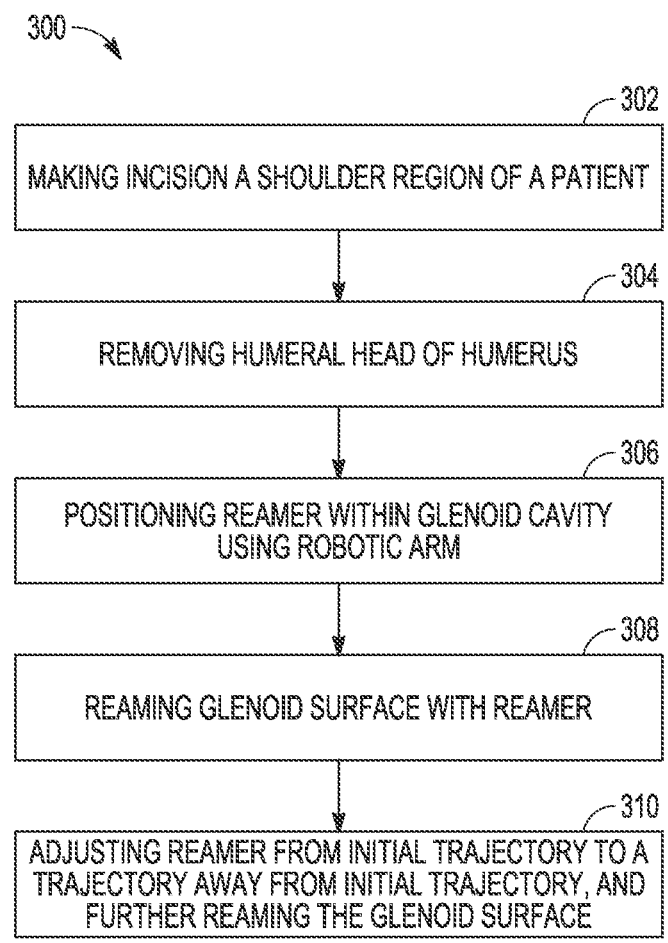
FIG. 9 illustrates a method of robotically controlling a reamer, in accordance with one example of the present application.

FIG. 9 illustrates a method 300 of robotically controlling a reamer, in accordance with one example of the present application. The steps or operations of the method 300 are illustrated in a particular order for convenience and clarity; many of the discussed operations can be performed by multiple different actors, devices, or systems. It is understood that subsets of the operations discussed in the method 300 can be attributable to a single actor, device, or system and can be considered a separate standalone process or method.

The method 300 includes an operation 302 to control movement of a robotic arm to position an end effector at a distal end of the robotic arm within a glenoid cavity of a patient.

The method 300 includes an operation 304 to activate a reamer affixed to the end effector to ream a glenoid surface of the patient within the glenoid cavity along a trajectory. After operation 304, the method 300 may proceed to optional operation 306 when a trajectory change is identified, or may proceed to operation 312. Operation 304 may include activating a cutting head of the reamer (e.g., at a distal end of the reamer). The cutting head may be configured to rotate about an axis of rotation without requiring use of a guide pin in a bone (e.g., the glenoid surface). This axis of rotation may differ from an axis of rotation for a primary driveshaft (e.g., offset and parallel to the primary driveshaft axis of rotation).

The method 300 includes an optional operation 306 to identify a change to the trajectory. Identifying the change may include receiving an indication of a change, for example on a user interface. In another example, identifying the change may be based on a current depth of the reamer or a preoperative plan.

The method 300 includes an optional operation 308 to control movement of the robotic arm to reposition the end effector according to the changed trajectory.

The method 300 includes an optional operation 310 to cause the reamer to ream the glenoid surface at the changed trajectory.

The method 300 includes an operation 312 to prevent overreaming by the reamer, using the robotic arm. In an example, operation 312 may be occurring during any or all operations 302-310. Operation 312 may include preventing overreaming based on a specified maximum depth. The specified maximum depth may be based on a diagnostic image of the glenoid surface. In an example, a diagnostic depth may be determined, which may then be automatically translated by processing circuitry to a frame of reference of the robotic arm based on a registration to a frame of reference of the diagnostic image.

Figure 10:
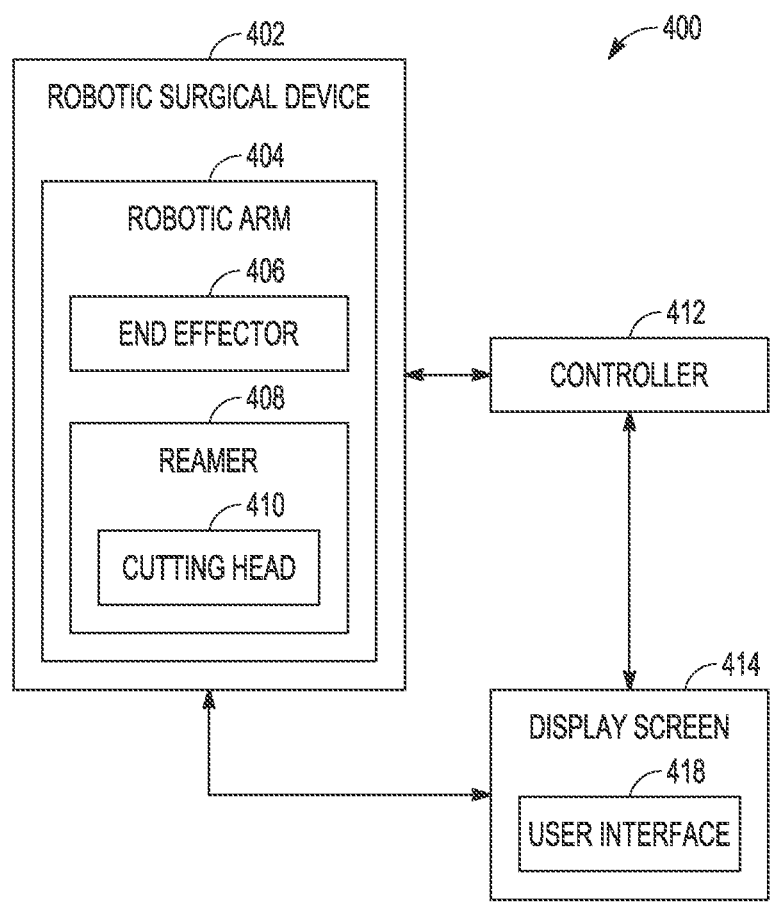
FIG. 10 illustrates a schematic view of a robotic surgical system for robotically assisted reaming, in accordance with at least one example of the present application.

FIG. 10 illustrates a schematic view of a robotic surgical system 400 for robotically assisted reaming, in accordance with at least one example of the present application. The robotic surgical system 400 includes a robotic surgical device 402, which can include a robotic arm 404, an end effector 406, such as to attach or manipulate a reamer 408 with a cutting head 410, or the like. The robotic arm 404 can be similar to the robotic arm 102 discussed above with respect to FIG. 1A, in that robotic arm 404 can be a movable and articulatable robotic arm. The end effector 406 can be similar to the end effector 100 discussed with respect to FIGS. 1A-6 above. The robotic arm 404 can move autonomously in an example. In another example, the robotic arm 404 can provide a force assist to surgeon or user guided movements. In yet another example, a combination of autonomous movement and force assist movement can be performed by the robotic arm 404 (e.g., force assist for an initial movement, and autonomously moving a later movement). In an example, the robotic arm 404 can resist an applied force. For example, the robotic arm 404 can be programmed to stay within a particular range of locations or a particular position, move at a particular speed (e.g., resist a higher speed by resisting force), or the like.

The robotic surgical device 402 can output or receive data from a controller 412. The controller 412 can be implemented in processing circuitry (e.g., hardwired or a processor), a programmable controller, such as a single or multi-board computer, a direct digital controller (DDC), a programmable logic controller (PLC), a system on a chip, a mobile device (e.g., cell phone or tablet), a computer, or the like. In one example, the controller 412 can output information to a display screen 414. The display screen 414 can retrieve and display information from an imaging camera. The imaging camera can be physically positioned on the robotic surgical device 402, such as on the robotic arm 404, the end effector 406, or the reamer 408 (e.g., on or near the cutting head 410, such as on housing of the cutting head 410). In an example, the display screen 414 can be used to display a user interface 418. In an example, the display screen 414 can be a touch screen display. In another example, user interface 418 on the display screen 414 can provide lights, buttons, or switches. A user can thereby interact with the display screen 414 and the user interface 418 to input control commands, which can be relayed to the robotic surgical device 402 through the controller 412 to control the robotic surgical device 402. The robotic surgical system 400 can be used to perform all, or a portion of, a surgical procedure on a patient.

In the operation of some examples, a user can interact with the user interface 418 on the display screen 414 to power on the robotic surgical device 402. Power can be indicated by a light, for example, on the user interface 418, or on the robotic arm 404. When the robotic surgical device 402 is powered on, the user can operate the robotic arm 404, end effector 406, and the reamer 408, including cutting head 410, by interacting with the display screen 414 and the user interface 418.

The robotic surgical system 400 can be used to ream a target bone surface of a patient, for example to prepare the bone surface to receive an implant, with the cutting head 410 of the reamer 408. In an example, a cutting angle or trajectory of the cutting head 410 can be changed intraoperatively, for example using the controller 412, in contrast to non-adjustable methods of guiding reamers, such a guide pin fixed to the bone. The robotic arm 404 can thereby allow a user to respond to specific bone conditions of a patient, to significantly improve the amount of a patient's bone that can be preserved during a joint replacement procedure. The bone penetration depth of the cutting head 410 can be precisely controlled using the robotic arm 404, in contrast to traditional hand-held reamers requiring a depth-stop, to prevent over-penetration.

The robotic surgical system 400 may be configured to use the reamer 408 to ream bone. The reamer 408 can be coupled to the end effector 406. The reamer 408 can include a primary driveshaft configured, for example, to rotate about a first axis of rotation. The cutting head 410 can be coupled to a distal end of the primary driveshaft. In an example, the cutting head 410 is configured to rotate about a second axis of rotation. The second axis of rotation can be parallel to and laterally offset from the first axis of rotation. The robotic arm 404 can be configured to robotically prevent overreaming by the reamer. For example, the controller 412 can receive a maximum depth or a depth range, identify a current depth, and prevent further depth movement by the robotic arm 404 when the current depth is at, exceeds, or approaches the maximum depth or the depth range. The depth range or the maximum depth can be determined preoperatively during a planning stage, in an example. The robotic arm 404 can prevent overreaming using a camera or ultrasonic transducer affixed to an end of the reamer 408 (e.g., at or near the cutting head 410 or on a housing thereof). The cutting head 410 can be configured to rotate about an axis of rotation without requiring use of a guide pin in the reamed bone. The robotic arm 404 can be configured to resist movement of the robotic arm 404 (e.g., to prevent translation or rotation by the reamer 408) from a force applied by a motor.

Figure 11:
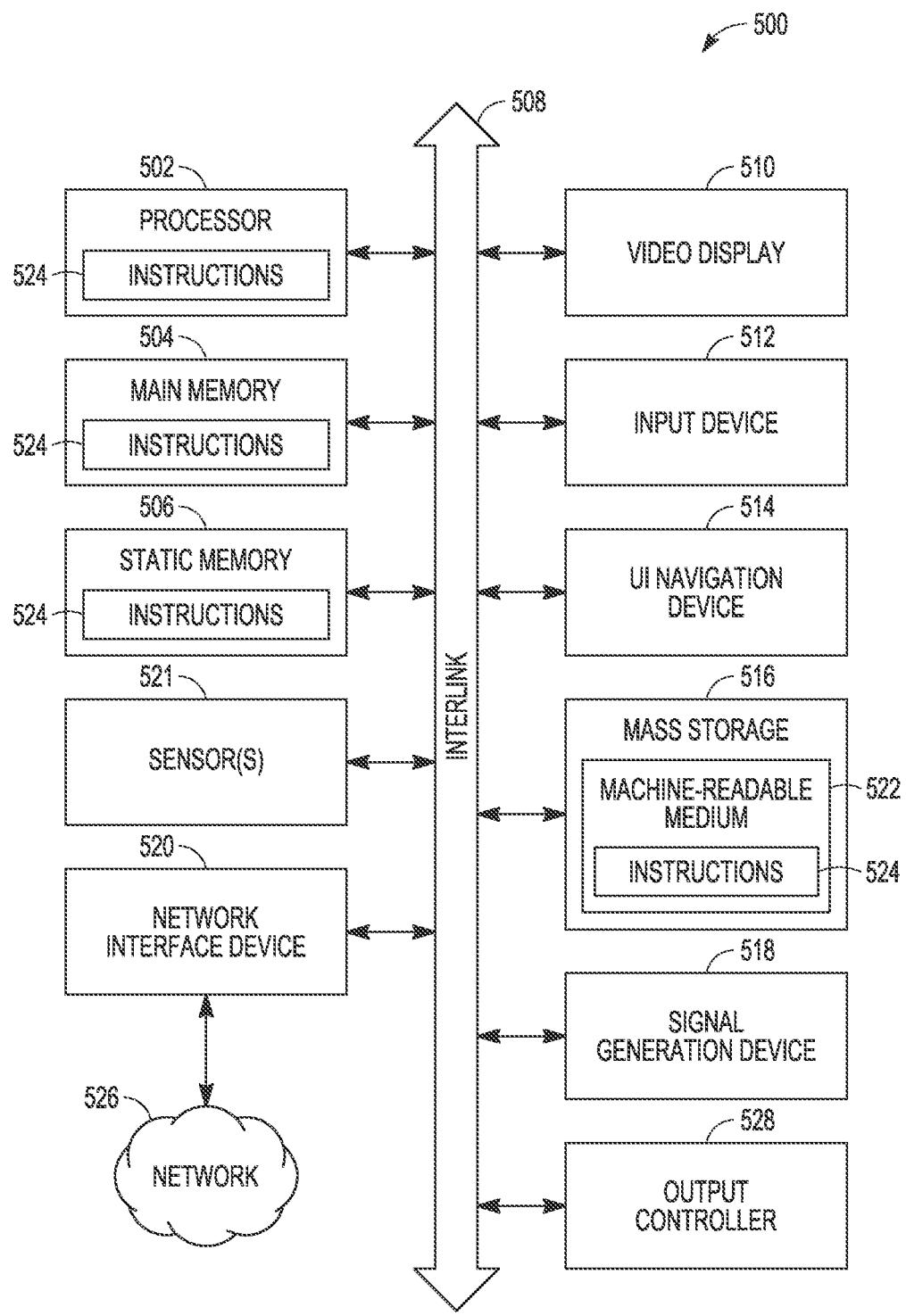
FIG. 11 illustrates a block diagram of an example machine upon which any one or more of the techniques discussed herein can be performed, in accordance with at least one example of the present application.

FIG. 11 illustrates a block diagram of an example machine 500 upon which any one or more of the techniques discussed herein can perform in accordance with some embodiments. In alternative embodiments, the machine 500 can operate as a standalone device or can be connected (e.g., networked) to other machines. In a networked deployment, the machine 500 can operate in the capacity of a server machine, a client machine, or both in server-client network environments. In an example, the machine 500 can act as a peer machine in peer-to-peer (P2P) (or other distributed) network environment.

The machine 500 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 500 can include a hardware processor 502 (e.g., a central processing unit (CPU), a graphics processing unit (GPU), a hardware processor core, or any combination thereof), a main memory 504 and a static memory 506, some or all of which can communicate with each other via an interlink (e.g., bus) 508. The machine 500 can further include a display unit 510, an alphanumeric input device 512 (e.g., a keyboard), and a user interface (UI) navigation device 514 (e.g., a mouse). In an example, the display unit 510, input device 512 and UI navigation device 514 can be a touch screen display. The machine 500 can additionally include a storage device (e.g., drive unit) 516, a signal generation device 518 (e.g., a speaker), a network interface device 520, and one or more sensors 521, such as a global positioning system (GPS) sensor, compass, accelerometer, or other sensors. The machine 500 can include an output controller 528, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 516 can include a machine readable medium 522 on which is stored one or more sets of data structures or instructions 524 (e.g., software) embodying or utilized by any one or more of the techniques or functions described herein. The instructions 524 can also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 can constitute machine readable media.

While the machine readable medium 522 is illustrated as a single medium, the term "machine readable medium" can include a single medium or multiple media (e.g., a centralized or distributed database, or associated caches and servers) configured to store the one or more instructions 524. The term "machine readable medium" can include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine-readable medium examples can include solid-state memories, and optical and magnetic media.

The instructions 524 can further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 can include one or more physical jacks (e.g., Ethernet, coaxial, or phone jacks) or one or more antennas to connect to the communications network 526. In an example, the network interface device 520 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

While the end effector has been discussed with regard to shoulder arthroplasty, the end effector of the present disclosure can be used in surgical procedures in a wide range of anatomical applications including knee, ankle, hip, or elbow procedures. The use of a robotic arm, together with the end effector, can eliminate the need for a guide pin, which can reduce the invasiveness of a joint replacement procedure for a patient. The offset reamer can provide a surgeon with the ability to view a patient's anatomy from directly above a cutting head, eliminating the need for a large incision to view a cutting head from the side. The robotic arm can provide increased accuracy, articulation, and precision over a fixedly attached guide pin, which can increase patient bone preservation to reduce trauma. These benefits can enable a surgeon to complete a shoulder joint replacement procedure with greater accuracy than existing devices and methods, to provide improved outcomes for a patient, such as increased repeatability, a shorter hospital stay, and a reduced recovery time.

NOTES AND EXAMPLES

The following, non-limiting examples, detail certain aspects of the present subject matter to solve the challenges and provide the benefits discussed herein, among others.

Example 1 is a robotically controlled reamer, the reamer comprising: a primary driveshaft configured to rotate about a first axis of rotation via a motor; a cutting head coupled to a distal end of the primary driveshaft, the cutting head configured to rotate about a second axis of rotation, parallel to and laterally offset from the first axis of rotation, and a cutting depth of the cutting head controllable by a robotic arm.

In Example 2, the subject matter of Example 1 includes, wherein the cutting depth of the cutting head is controlled by limiting movement of the robotically controlled reamer to less than a preoperatively specified cutting depth.

Example 3 is a robotic surgical system comprising: a reamer operable to ream bone coupled to an end effector, the reamer comprising: a primary driveshaft configured to rotate about a first axis of rotation; a cutting head coupled to a distal end of the primary driveshaft, the cutting head configured to rotate about a second axis of rotation, parallel to and laterally offset from the first axis of rotation; and a robotic arm including the end effector, the robotic arm configured to control a cutting depth of the cutting head.

In Example 4, the subject matter of Example 3 includes, wherein the robotic arm is configured to control the cutting depth of the cutting head by controlling movement of the reamer within a specified cutting depth range, the specified cutting depth range identified via preoperative planning.

In Example 5, the subject matter of Examples 3-4 includes, wherein the robotic arm is configured to control the cutting depth of the cutting head by using a camera affixed to the cutting head.

In Example 6, the subject matter of Examples 3-5 includes, wherein the cutting head is configured to rotate about the second axis of rotation without requiring use of a guide pin in the reamed bone.

In Example 7, the subject matter of Examples 3-6 includes, wherein the robotic arm is further configured to resist movement of the robotic arm from torque applied by the motor.

Example 8 is a reamer for shaping a bone without requiring a guide pin, the reamer comprising: a primary driveshaft configured to rotate about a first axis of rotation; a cutting head coupled to a distal end of the primary driveshaft, the cutting head configured to rotate about a second axis of rotation laterally offset from the first axis of rotation.

In Example 9, the subject matter of Example 8 includes, wherein the second axis of rotation is parallel to the first axis of rotation.

In Example 10, the subject matter of Examples 8-9 includes, wherein the orientation of the primary driveshaft is adjustable relative to the orientation of the cutting head, such that the first axis of rotation is located at an acute or an oblique angle relative to the second axis of rotation.

In Example 11, the subject matter of Examples 8-10 includes, a motive coupler coupled to the primary driveshaft, the motive coupler engageable with a motive source to provide rotary motion to the primary driveshaft, at least a portion of the motive coupler and the primary driveshaft rotatable about the first axis of rotation.

In Example 12, the subject matter of Example 11 includes, wherein the motive source is an electric motor, the motor operable to rotate the primary driveshaft to rotate the cutting head.

In Example 13, the subject matter of Examples 11-12 includes, wherein the motive source is a pneumatically-actuated motor, the motor operable to rotate the primary driveshaft to rotate the cutting head.

In Example 14, the subject matter of Examples 8-13 includes, a retainer connecting the primary driveshaft to an end effector of a robotic arm, a portion of the retainer being laterally offset from both the end effector and the reamer.

In Example 15, the subject matter of Examples 8-14 includes, a secondary driveshaft coupled to the cutting head, the secondary driveshaft rotatable about a third axis of rotation that is not parallel to the first axis of rotation or the second axis of rotation.

In Example 16, the subject matter of Examples 8-15 includes, a camera coupled to a distal portion of a housing of the primary driveshaft.

Example 17 is a method of robotically controlling a reamer comprising: using processing circuitry, controlling movement of a robotic arm to position an end effector at a distal end of the robotic arm within a glenoid cavity of a patient; activating a reamer affixed to the end effector to ream a glenoid surface of the patient within the glenoid cavity along a trajectory; identifying a change to the trajectory; controlling, using the processing circuitry, movement of the robotic arm to reposition the end effector according to the changed trajectory; and causing the reamer to ream the glenoid surface at the changed trajectory.

In Example 18, the subject matter of Example 17 includes, wherein the change to the trajectory is received via a user interface.

In Example 19, the subject matter of Example 18 includes, wherein the change to the trajectory is determined automatically based on a preoperative plan.

Example 20 is a method of robotically controlling a reamer comprising: using processing circuitry, controlling movement of a robotic arm to position an end effector at a distal end of the robotic arm within a glenoid cavity of a patient; activating a reamer affixed to the end effector to ream a glenoid surface of the patient within the glenoid cavity along a trajectory; and controlling a cutting depth of the reamer, using the robotic arm, based on a specified maximum cutting depth.

In Example 21, the subject matter of Example 20 includes, wherein the maximum cutting depth is determined preoperatively based on a diagnostic image of the glenoid surface and automatically translated by the processing circuitry to a frame of reference of the robotic arm based on a registration to a frame of reference of the diagnostic image.

In Example 22, the subject matter of Examples 20-21 includes, wherein activating the reamer includes activating a cutting head of the reamer.

In Example 23, the subject matter of Example 22 includes, wherein activating the cutting head includes controlling a motor to rotate the cutting head about an axis of rotation without requiring use of a guide pin in the glenoid surface.

Example 24 is at least one machine-readable medium including instructions that, when executed by processing circuitry, cause the processing circuitry to perform operations to implement of any of Examples 1-23.

Example 25 is an apparatus comprising means to implement of any of Examples 1-23.

Example 26 is a system to implement of any of Examples 1-23.

Example 27 is a method to implement of any of Examples 1-23.

What is claimed is:

1. A robotically controlled reamer, the reamer comprising:
a primary driveshaft configured to rotate about a first axis of rotation via a motor;
a cutting head coupled to a distal end of the primary driveshaft, the cutting head configured to rotate about a second axis of rotation, parallel to and laterally offset from the first axis of rotation, and a cutting depth of the cutting head controllable by a robotic arm; and
a retainer including a distal end configured for coupling to the primary driveshaft and a proximal end configured for coupling to the robotic arm, the retainer including a first portion defining a first longitudinal axis extending orthogonally to the primary driveshaft, the retainer including a second portion located distal to the first portion and defining a second longitudinal axis extending parallel to and laterally offset from the first longitudinal axis, the second portion being monolithically formed with the first portion such that the second portion remains in a fixed position relative to the first portion.

2. The robotically controlled reamer of claim 1, further comprising the robotic arm and the end effector.

3. The robotically controlled reamer of claim 1, wherein the proximal end of the retainer is aligned with the first longitudinal axis.

4. The robotically controlled reamer of claim 3, wherein the distal end of the retainer is aligned with the first longitudinal axis.

5. The robotically controlled reamer of claim 4, wherein the second portion of the retainer defining the second longitudinal axis comprises an offset segment connected to and extending from the first portion.

6. A robotic surgical system comprising:
a reamer operable to ream bone coupled to an end effector, the reamer comprising:
 a primary driveshaft configured to rotate about a first axis of rotation;
 a cutting head coupled to a distal end of the primary driveshaft, the cutting head configured to rotate about a second axis of rotation, parallel to and laterally offset from the first axis of rotation;
a robotic arm including the end effector, the robotic arm configured to control a cutting depth of the cutting head; and
a retainer including a distal end configured for coupling to the primary driveshaft and a proximal end configured for coupling to the robotic arm, the retainer including a first portion defining a first longitudinal axis extending orthogonally to the primary driveshaft, the retainer including a second portion located distal to the first portion and defining a second longitudinal axis extending parallel to and laterally offset from the first longitudinal axis, the second portion being monolithically formed with the first portion such that the second portion remains in a fixed position relative to the first portion.

7. The robotic surgical system of claim 6, wherein the robotic arm is configured to control the cutting depth of the cutting head by controlling movement of the reamer within a specified cutting depth range, the specified cutting depth range identified via preoperative planning.

8. The robotic surgical system of claim 6, wherein the robotic arm is configured to control the cutting depth of the cutting head by using a camera affixed to the cutting head.

9. The robotic surgical system of claim 6, wherein the cutting head is configured to rotate about the second axis of rotation without requiring use of a guide pin in the reamed bone.

10. The robotic surgical system of claim 6, wherein the robotic arm is further configured to resist movement of the robotic arm from torque applied by the motor.

11. The robotic surgical system of claim 6, wherein the proximal end of the retainer is aligned with the first longitudinal axis.

12. The robotic surgical system of claim 11, wherein the distal end of the retainer is aligned with the first longitudinal axis.

13. The robotic surgical system of claim 12, wherein the second portion of the retainer defining the second longitudinal axis comprises an offset segment connected to and extending from the first portion.

\* \* \* \* \*